US00PP33491P2

(12) United States Plant Patent
Kordes

(10) Patent No.: US PP33,491 P2
(45) Date of Patent: Sep. 21, 2021

(54) MINIATURE ROSE PLANT NAMED 'KORPOT106'

(50) Latin Name: *Rosa hybrida*
Varietal Denomination: KORpot106

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 17/136,129

(22) Filed: Dec. 29, 2020

(51) Int. Cl.
*A01H 5/02* (2018.01)
*A01H 6/74* (2018.01)

(52) U.S. Cl.
USPC ..... Plt./121
CPC ..... *A01H 6/749* (2018.05)

(58) Field of Classification Search
USPC ..... Plt./121
CPC ..... A01H 6/749
See application file for complete search history.

(56) References Cited

U.S. PATENT DOCUMENTS

PP29,042 P3 3/2018 Kordes

*Primary Examiner* — Anne Marie Grunberg
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot106', is disclosed. The new variety forms abundantly on a substantially continuous basis attractive, hot pink colored blossoms. Attractive vigorous vegetative is formed, which contrasts beautifully with the blossoms. The growth habit is compact. The new variety is well suited for providing attractive ornamentation in the landscape.

1 Drawing Sheet

Botanical/commercial classification:
Latin name: *Rosa hybrida.*
Varietal denomination: 'KORpot106'.

CROSS-REFERENCE TO RELATED APPLICATIONS

This application claims priority to Plant Breeders' Right Application Number 2020/2367, which was filed at Community Plant Variety Office in the European Union on Sep. 27, 2020, the contents of which are hereby incorporated by reference for all purposes.

SUMMARY OF THE INVENTION

The new variety of *Rosa hybrida* Miniature Rose Plant of the present invention was created during 2015 at Offenseth-Sparrieshoop, Germany by artificial pollination wherein two parents were crossed which previously had been studied in the hope that they would contribute the desired characteristics. The female parent (i.e., seed parent) of the new variety was the 'KORpot064' variety (U.S. Plant Pat. No. 29,042). The male parent (i.e., pollen parent) was an unnamed seedling (non-patented).

The parentage can be summarized as follows:

'KORpot064' x unnamed seedling

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) displays attractive, hot pink colored blossoms,
(b) exhibits a compact growth habit, and
(c) forms vigorous vegetation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'KORpot064' variety (i.e., the seed parent) displays less bright pink flower color and a less compact growth habit compared to the new variety. In addition, the unnamed seedling male parent (i.e., the pollen parent) displays less compact growth habit compared to the new variety and the new variety has an improved shelf life compared to the pollen parent variety. Moreover, the new variety can be readily distinguished from other similar non-parental varieties. For example, the 'KORdatiffi' variety (non-patented) displays less bright pink colored flowers and forms blooms in a cluster, whereas the new variety displays brighter pink colored flowers and forms blooms solitarily.

The new variety has been found to undergo asexual propagation in Klein Offenseth-Sparrieshoop, Germany by a number of routes, such as vegetative cuttings. Asexual propagation techniques in Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot106'.

The new variety was first offered for sale on January, 2020 by the inventor or another who obtained the new variety directly or indirectly from the inventor.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Odense, Denmark while growing indoors on its own roots in a 10.5 cm container.

Drawing—illustrates a specimen of a plant displaying floral buds and flowers at varying points of opening.

DETAILED BOTANICAL DESCRIPTION

The chart used in the identification of colors is that of The Royal Horticultural Society (R.H.S. Colour Chart, 1966 edition). The terminology which precedes reference to the chart has been added to indicate the corresponding color in more common terms. The description is based on the observation of a one-year-old specimen of the new variety, observed during October, while growing in a one-gallon container on its own roots in a greenhouse in Cochranville, Pa.

Commercial classification: Miniature Rose Plant.

Plant:

*Habit*.—Compact.

*Height*.—Approximately 24.0 cm on average.

*Width*.—Approximately 22.0 cm on average.

Branches:

*Stem color*.—Commonly near Green Group 137C.

*Length*.—Main stems: approximately 24.0 cm on average. — secondary stems: approximately 9.0 cm on average.

*Texture*.—Glabrous.

*Thorns*.—Young thorns: moderate; color is commonly near Greyed-Yellow Group 160B; length is approximately 5.0 mm on average; and width is approximately 2.0 mm on average at point of attachment.

Foliage:

*Young foliage color*.—Upper surface: commonly near Green Group 137A with indistinguishable venation. — under surface: commonly a blend of near Yellow-Green Group 146B and near Greyed-Orange Group 176C, with venation of near Green Group 138A.

*Old foliage color*.—Upper surface: commonly near Green Group 139A with venation of near Green Group 1376. — under surface: commonly near Green Group 1396 with venation of near Green Group 139C.

*Petiole*.—Upper surface: texture is smooth; color is commonly near Green Group 137A. — under surface: texture is mostly smooth with sparse prickles, color is commonly near Green Group 138A.

*Rachis*.—Color: upper surface is commonly near Green Group 137A, under surface is commonly near Green Group 138A.

*Stipules*.—Length: approximately 7.0 mm on average. — width: approximately 3.0 mm on average. — margin: entire to erose. — color: upper surface is commonly near Green Group 1386, under surface is commonly near Green Group 138C.

5-*leaflet leaf length*.—Approximately 8.0 cm on average. — width: approximately 4.5 cm on average.

*Leaflet arrangement*.—Odd-pinnate.

Leaflets:

*Number of leaflets*.—3, 5, and 7.

*Shape*.—Ovate; apex is acute; and base is rounded.

*Leaflet margin*.—Serrate.

*Glossiness of upper side of leaflet*.—Glossy.

*Venation pattern*.—Reticulate.

*Texture*.—Upper and under surfaces is smooth.

*Terminal leaflet*.—Length: approximately 3.5 cm on average. — width: approximately 1.8 cm on average.

*Lower leaflet*.—Length: approximately 2.0 cm on average. — width: approximately 1.5 cm on average.

Inflorescence:

*Number of flowers*.—Generally about 7 blooms on average on a plant at once.

*Number of blooms per stem*.—Typically 1 bloom per stem on average.

*Peduncle*.—Length: approximately 3.5 cm on average. — diameter: approximately 3.0 mm on average. — surface texture: glabrous. — strength: strong. — color: commonly near Yellow-Green Group 144A.

*Sepals*.—Number: commonly 5. — length: approximately 1.5 cm on average. — width: approximately 0.5 cm on average. — margin: entire with occasional extensions on two or three sepals measuring approximately 7.0 mm in length on average and 2.0 mm in width on average. — upper surface color and texture: commonly near Yellow-Green Group 144A; covered in short pubescence. — under surface color and texture: commonly near Yellow-Green Group 144A; puberulent. — shape: lanceolate. — apex: acute to aristate. — base: truncate or flat as it joins the receptacle.

*Bud*.—Shape: globular to ovoid. — length: approximately 2.0 cm on average. — width: approximately 2.0 cm on average. — color: when opening: commonly near Red-Group 55A.

*Flower*.—Diameter: approximately 4.5 cm on average. — height: approximately 2.0 cm on average. — duration: flower is on the plant approximately 28 days. — form: double, cuplike. — profile: flat. — number of petals under normal conditions: approximately 85 petals on average. — shape of the petal: overall: broadly obovate. apex: rounded to cuspidate. base: rounded to cuneate. — petal length: inner petals are approximately 1.0 cm on average, outer petals are approximately 2.0 cm on average. — petal width: inner petals are approximately 8.0 mm on average, outer petals are approximately 2.0 cm on average. — petal margin: entire. — petal drop: average for the type. — fragrance: very light sweet fragrance. — petal color when first and fully open: upper surface: commonly near Red-Purple Group 62A with basal spot of commonly near Greyed- Yellow Group 160D. under surface: commonly near Red-Purple Group 65A with basal spot of commonly near Green-White Group 157A. — petal color when fading: upper and under surfaces: commonly near White Group 155C. — petal texture: upper and lower surfaces are glabrous. — petaloids: typically 7 per flower; color of upper surface is commonly near Red-Purple Group 65B with basal spot of near Yellow Group 4D, under surface is commonly near Red-Purple Group 65B with basal spot of near Yellow Group 4D; length is approximately 5.0 mm on average; width is approximately 3.0 mm on average; texture is smooth; margin is variable, entire to erose; shape is rounded and mostly curving inward; apex is round; base is cuneate.

*Receptacle*.—Color: commonly near Yellow-Green Group 145B. — diameter: approximately 5.0 mm on average. — surface texture: smooth. — shape: urn shaped.

*Stamen*.—Number is approximately 50 on average. — anthers: number is approximately 50 on average; color is commonly near Yellow Group 2B; length is approximately 1.5 mm on average; and shape is oval. — filaments: length is approximately 1.5 mm on average and color is commonly near Yellow Group 10B.

*Pistils*.—Arrangement is separate and free; number is approximately 96 on average. — styles: length is approximately 5.0 mm on average and color is commonly near Yellow Group 5B at the base, transitioning to Red Group 45D at the apex. — stigmas: diameter is typically less than 1.0 mm; color is commonly near Yellow-Green Group 149B; shape is fan shaped.

*Pollen*.—None observed.

*Hips*.—None observed.

Development:

*Vegetation*.—Dark green, vigorous and strong.

*Blooming*.—Abundant and continuous.

*Hardiness*.—Unknown.

*Resistance to disease*.—Good resistance to Powdery Mildew (*Sphaerotheca pannosa*) disease under normal greenhouse growing conditions in Cochranville, Pa.

*Pest resistance/susceptibility*.—None observed to date.

Plants of the 'KORpot106' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) displays attractive, hot pink colored blossoms, (b) exhibits a compact growth habit, and (c) forms vigorous vegetation;

substantially as herein shown and described.

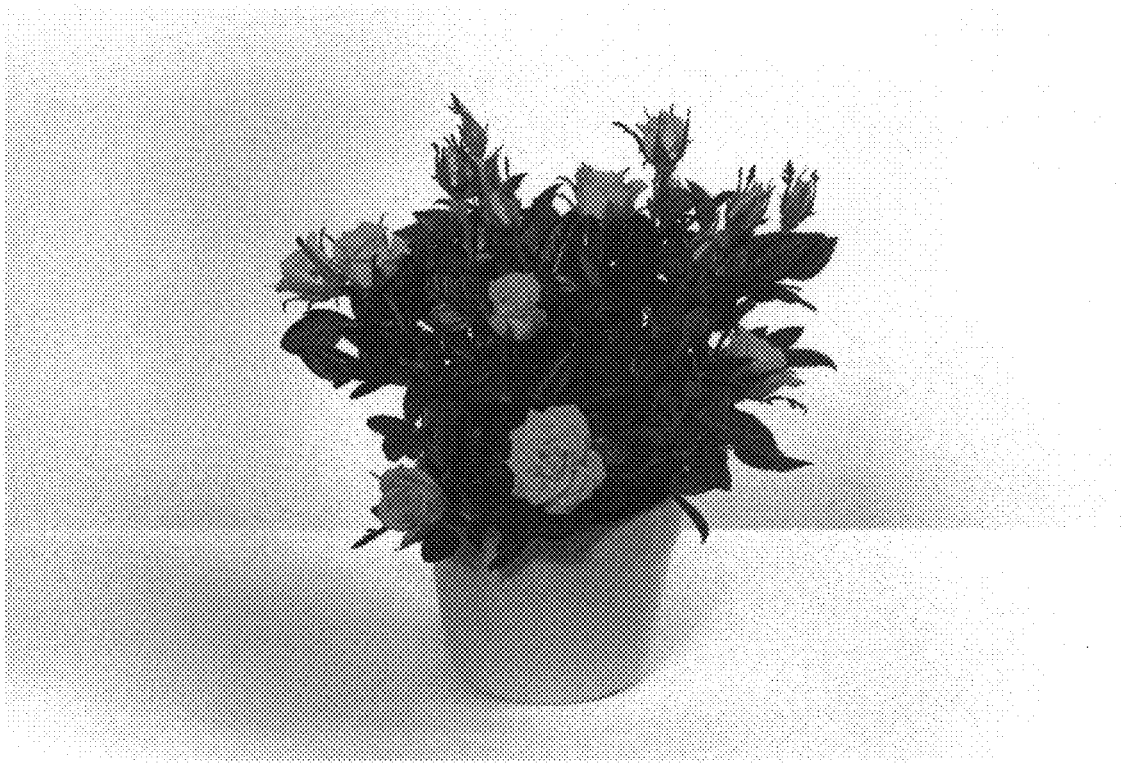

* * * * *